United States Patent
Revesz et al.

(10) Patent No.: US 6,566,637 B1
(45) Date of Patent: May 20, 2003

(54) MICROWAVE ASSISTED CONTENT ANALYZER

(75) Inventors: Robert N. Revesz, Monroe, NC (US); James E. Thomas, Harrisburg, NC (US); Wyatt P. Hargett, Jr., Matthews, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 09/605,816

(22) Filed: Jun. 28, 2000

(51) Int. Cl.⁷ .................................................. H05B 6/64
(52) U.S. Cl. ........................ 219/679; 219/702; 219/708; 219/710; 219/711
(58) Field of Search ................................ 219/679, 771, 219/759, 710, 711, 702; 73/76, 1.13; 374/150, 110, 14, 149; 177/1, 25.13, 245, 145

(56) References Cited

U.S. PATENT DOCUMENTS

| | | |
|---|---|---|
| 4,276,948 A | 7/1981 | Nichols |
| 4,438,500 A | 3/1984 | Collins et al. |
| 4,457,632 A | 7/1984 | Collins et al. |
| 4,589,782 A * | 5/1986 | Park .............................. 374/14 |
| 4,681,996 A | 7/1987 | Collins et al. |
| 5,365,043 A | 11/1994 | Bradford |
| 5,402,672 A | 4/1995 | Bradford |
| 5,736,716 A | 4/1998 | Kim et al. |
| 5,796,080 A | 8/1998 | Jennings et al. |
| 5,988,877 A * | 11/1999 | Hochrad et al. ............ 374/150 |
| 6,017,147 A | 1/2000 | Gibson, Jr. |
| 6,084,226 A * | 7/2000 | Greene et al. ............... 219/718 |
| 6,086,826 A * | 7/2000 | Thomas et al. ............... 422/102 |
| 6,227,041 B1 * | 5/2001 | Collins et al. .................. 73/76 |
| 6,268,570 B1 * | 7/2001 | McLendon et al. ............ 177/1 |

FOREIGN PATENT DOCUMENTS

| | | |
|---|---|---|
| EP | 0344465 A2 | 12/1989 |
| EP | 0383344 A2 | 8/1990 |
| JP | 58165038 | 9/1983 |
| JP | 60219545 | 11/1985 |
| WO | WO99/49310 A1 | 9/1999 |
| WO | WO99/54035 A1 | 10/1999 |
| WO | WO00/16067 A1 | 3/2000 |

OTHER PUBLICATIONS

North Atlantic Equipment Sales, Inc. Brochure entitled "Now with an internal balance. North Atlantic's MMA–91(TM) is a Microwave Drying Revolution"; Wappingers Falls, NY.

* cited by examiner

Primary Examiner—Teresa Walberg
Assistant Examiner—Quang Van
(74) Attorney, Agent, or Firm—Summa & Allan, P.A.

(57) ABSTRACT

A method and associated apparatus are disclosed for microwave assisted content analysis. The method includes the steps of applying microwave radiation to a sample while concurrently rotating the sample while the microwave radiation is being applied and while concurrently weighing the sample and while measuring the temperature of the sample and controlling or moderating the microwaves applied to the sample based upon the measured temperature.

26 Claims, 5 Drawing Sheets

MICROWAVE ASSISTED CONTENT ANALYZER

FIELD OF THE INVENTION

The present invention relates to the content analysis of materials. In particular, it relates to the use of microwave radiation to assist in moisture content analysis and related techniques in materials with compositions that are less responsive to the effects of microwave radiation.

BACKGROUND OF THE INVENTION

The present invention relates to the content analysis of materials. Because the contents or compositions of materials give those materials their particular properties, knowing such content can be particularly important for purposes of making, using, processing, or otherwise dealing with various materials.

The techniques used to analyze the contents of various materials are almost endless. The present invention relates particularly to moisture content analysis, and has secondary, but important aspects related to the measurement of other materials in a sample, such as (but not limited to) fats and oils, and volatiles other than water. Foods are a particularly useful example of materials for which knowledge of moisture content is quite valuable, and some cases required (e.g. many statutory and regulatory schemes apply to the content and labeling of food products). Accordingly, a number of techniques have been developed for measuring the moisture content of materials and particularly the moisture content of foods. In a conventional technique referred to as gravimetric moisture analysis, a sample is weighed, dried, and then reweighed. Comparing the two weights gives an absolute weight loss, which, if the material has not degraded, can be used to calculate and express the moisture content as a percentage.

Heat (often convection heating) is typically used to accelerate the removal of moisture from materials in gravimetric analysis techniques. The use of a typical oven or a hotplate for such purposes, however, raises a number of associated problems or difficulties. First, if heat tends to degrade the material, rather than merely drive off the moisture, the technique is unsuitable for moisture content analysis of that material. Additionally, because heated samples create air currents that can affect the output readings of sophisticated balances, heated drying techniques require relatively long waiting periods between measurements, with the measurement having to be repeated until the dried weight remains constant.

In more recent developments, microwaves have been used to drive moisture from samples and thus assist in the gravimetric analysis of such materials. This technique has worked extremely-well in a number of circumstances, and appropriate moisture analyzers using microwave techniques have been available for some years, e.g., U.S. Pat. Nos. 4,438,500 and 4,457,632.

Furthermore, various improvements continue to make the use of microwave assisted techniques more feasible for more and more difficult materials. Again using food as the example, items with relatively high fat content (such as cheese and other dairy products) or low moisture content (e.g., powdered milk) can be difficult to analyze (for moisture content) using microwave techniques because they tend to cook or degrade when heated, rather than simply give up moisture.

Exemplary improvements in microwave techniques for such purposes are set forth in co-pending and commonly assigned applications Ser. No. 09/398,129 filed Sep. 17, 1999 for "High Efficiency Cavity Design" (now U.S. Pat. No. 6,320,170); Ser. No. 09/397, 825, also filed Sep. 17, 1999 for "High Efficiency Air Shield" (now U.S. Pat. No. 6,302,577); Ser. No. 09/398,130 filed Sep. 17, 1999 for "Method for Correcting Weight Measurement Errors During Microwave Heating" (now U.S. Pat. No. 6,268,570); and Ser. No. 09/156,086 filed Sep. 17, 1998 for "Method and Apparatus for Measuring Volatile Content" (now U.S. Pat. No. 6,227,041). All describe improvements in methods, apparatus, and techniques for moisture and related content analysis of materials that are otherwise difficult to handle using microwave-assisted techniques. The contents of each of these pending applications are incorporated entirely herein by reference.

The most effective microwave heating of various materials tends to depend upon the presence of free moisture in the material to be heated. Thus, for samples with little or no free water, microwave heating is difficult or ineffective. In this regard a microwave apparatus incorporating a microprocessor can monitor the drying curve (weight loss v. time) of a sample and can predict the final dry weight (or moisture content) based on an initial portion of the drying curve. Such analyses usually may be conducted in about two to three minutes for samples that contain free water Nevertheless, some or all of the moisture present in low moisture content materials, such as dried milk powder and detergents, tends to be bound water (e.g. water of hydration) or for other reasons resists removal by microwave radiation. In such cases, applying microwave radiation solely to the sample tends to be generally unsatisfactory and often unsuccessful, particularly when such materials tend to burn or degrade before all of the moisture (bound or free) has been removed.

Accordingly, techniques have been incorporated in which a sample is placed on a material that absorbs microwaves and becomes heated in response to those microwaves. U.S. Pat. No. 4,681,996 is an example of one such technique. As set forth therein, the goal is for the thermally-responsive support to conductively heat the sample to release the bound water. Theoretically, a truly synergistic effect should be obtained because the thermally heated support in turn heats the sample to remove bound water while the free water responds to, and is removed by, the direct effect of the microwaves upon it.

Additionally, when non-polar solvents are present with bound or free water in a material to be analyzed for volatiles, they are likewise volatilized by the thermal heat from the support, while free water (which may have been thermally freed from a bound form), is vaporized by the microwave radiation. Thus, volatiles are quickly removed from the sample whether the volatiles are bound water, free water, other polar materials or non-polar compounds.

The techniques set forth in the '996 patent, however, are less successful in actual practice. As one disadvantage, the supports described therein are self-limiting in temperature response to microwaves, and thus pads of different composition are required for different desired temperatures. As another, the device and method failed to successfully address the differences in measured weight caused when air density gradients affected the internal balance. As a third disadvantage, no technique other than the self-limitation of the pad was available for measuring or controlling the temperature of the sample during the overall process, and the predictability of the pad's temperature was erratic. As known to those familiar with content analysis, certain standardized drying tests are based on a "loss-on-drying" measurement in which a sample is heated to and maintained at a specified temperature for a specified time. The weight loss under such conditions provides useful and desired information, provided the test is run under the specified conditions. Thus, absent temperature control, microwave techniques cannot be used for loss-on-drying analysis.

Accordingly, it remains a goal of this industry to continue to improve the apparatus and techniques under which content analysis can be carried out using microwave-assisted techniques, and can be done so for materials that are otherwise less responsive, or even non-responsive, to microwave radiation.

OBJECT AND SUMMARY OF THE INVENTION

Therefore, it is an object of the invention to provide an improvement in microwave-assisted techniques for content analysis.

The invention meets this object with a method of microwave-assisted content analysis. The method includes the steps of applying microwave radiation to a sample and susceptor pad while concurrently rotating the sample and pad while the microwave radiation is being applied, while concurrently weighing the sample, while measuring the temperature of the sample and pad, and while (if necessary or desired) moderating the microwaves being applied in response to the measured temperature.

In another aspect, the invention is an apparatus for microwave-assisted content analysis. The apparatus includes a source of microwave radiation, a cavity in microwave communication with said source, a balance with at least its pan (or pan equivalent) in said cavity, and means for rotating said balance pan within said cavity while concurrently measuring the weight of a sample on said pan.

In yet another aspect, the invention is a susceptor for microwave assisted content analysis that complements the method and apparatus. The susceptor is a pad formed of a blend of a first material dispersed in a second material, the first material being a material that generates heat in response to microwave radiation, and the second material being nonresponsive to microwave radiation, but conductively heated by said first material so that exposing said susceptor to microwave radiation evenly heats said pad and a sample on said pad.

These and other objects and advantages of the present invention will become clearer when taken in conjunction with the following detailed description and the accompanying drawings in which:

DETAILED DESCRIPTION OF THE PREFERRED EMBODIMENTS

In the first aspect, the invention is a method of microwave-assisted content analysis that comprises applying the microwave radiation to a sample on a susceptor pad while concurrently rotating the sample while the microwave radiation is being applied, while concurrently weighing the sample, while measuring the temperature of the rotating sample and pad, and moderating the applied microwave radiation in response to the measured temperature. In preferred embodiments, the method comprises maintaining the balance accuracy within about 10 milligrams (mg) while concurrently weighing and rotating the sample. In more preferred embodiments the method comprises maintaining the balance accuracy within 1 milligram, and in the most preferred embodiments, the method comprises maintaining the balance accuracy within 0.1 milligram.

Preferably, the method comprises rotating the sample on a sample pad—most preferably on the susceptor described below—at a speed of rotation that is sufficient to maintain an equilibrium temperature, or a equilibrium rate of temperature change, in a sample on the pad being rotated (or in the temperature of the sample and pad), but less than a speed at which the sample would become dislodged from the pad (usually by centrifugal force) or at which the desired accuracy of the balance would be reduced. Generally speaking, rotating the balance at higher speeds lowers the balance accuracy. Accordingly, in more preferred embodiments the method comprises rotating the sample pad at a speed of less than about 30 revolutions per minute (rpm), and in the most preferred embodiments the method comprises rotating the sample on the susceptor at a speed of between about 5 and 20 revolutions per minute.

In a manner consistent with good practices in microwave assisted chemistry and content analysis, the microwaves are preferably generated at the source, transmitted through a waveguide that is in communication with the source, and then transmitted from the waveguide to a cavity that contains the sample.

In order to control the temperature of the sample and pad, the invention incorporates the infrared temperature detection technique set forth in previously-incorporated Ser. No. 09/156,086, and the microwave power moderation techniques set forth in Ser. No. 09/063,545 (incorporated by reference below), or alternatively the microwave moderation technique set forth in commonly assigned U.S. Pat. No. 5,796,080 which is likewise incorporated entirely herein by reference.

Figure 1:
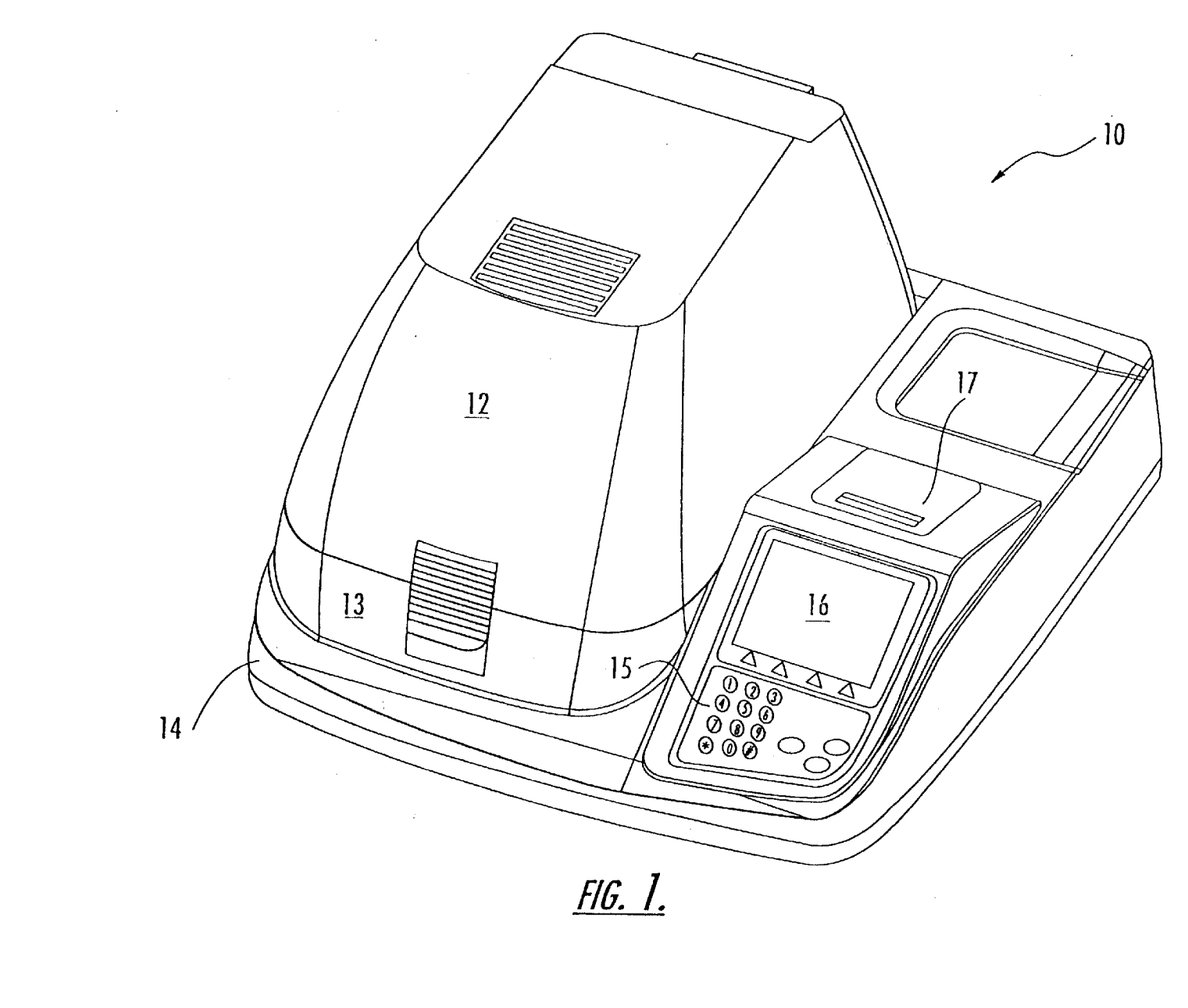
FIG. 1 is a perspective view of an apparatus according to the present invention.

FIG. 1 illustrates a commercial embodiment of the present invention broadly designated at 10. In the illustrated embodiment, the microwave content analyser 10 includes a cover portion 12 and a base portion 13 which together rest on an operative pedestal 14 that contains some of the electronics as will be described with respect to FIG. 2. Because the content analyser 10 of the present invention can usefully incorporate a processor for carrying calculations on the measurements made by the content analyser 10, the analyser 10 includes a keypad 15 and display 16 for input and output of appropriate data or instrument settings. A paper tape drive 17 is also included and provides a print out of appropriate results. Additional features of the invention and the content analyser in particular are set forth in those references previously incorporated herein.

Figure 2:
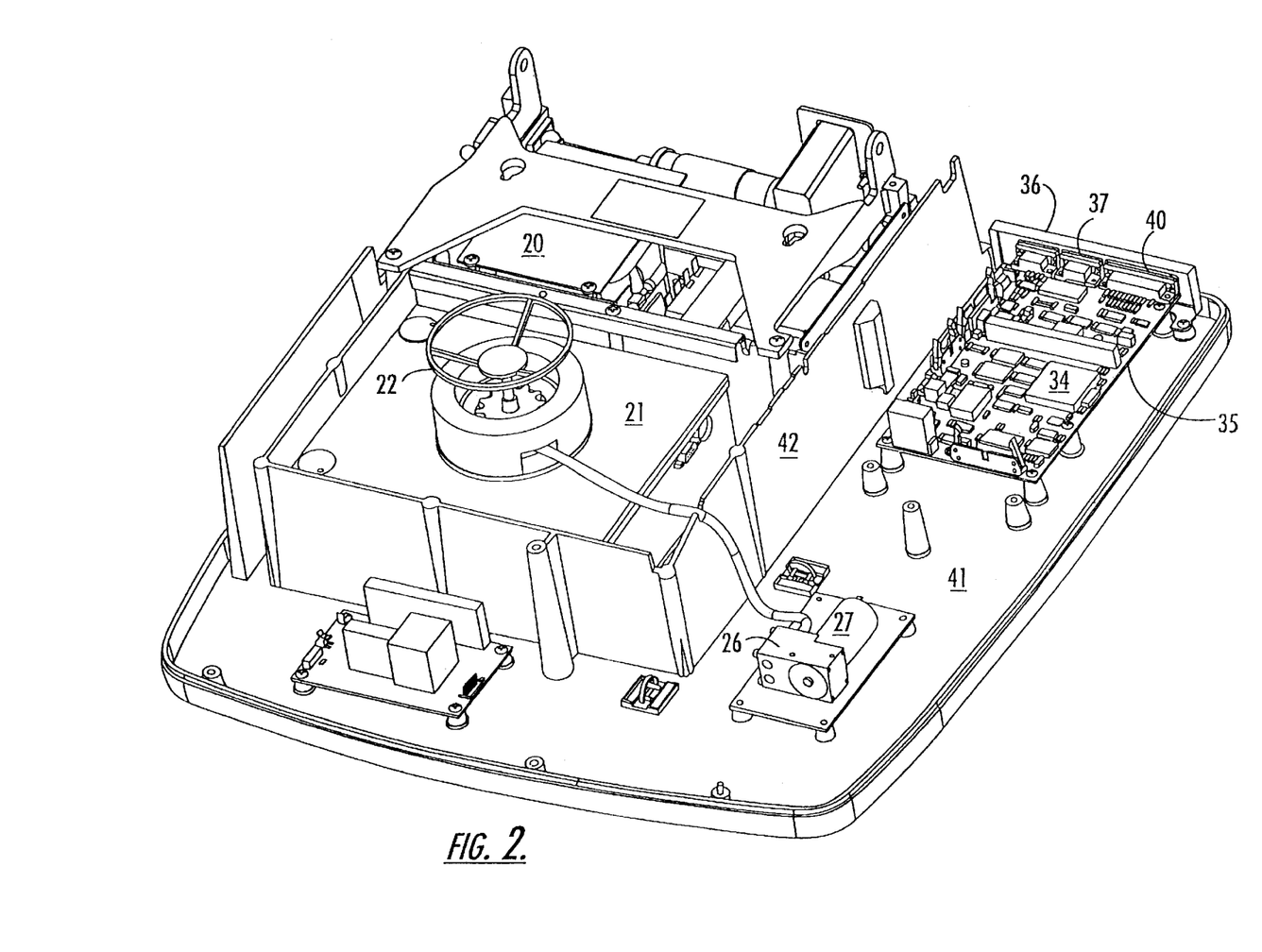
FIG. 2 is a perspective view of the apparatus according to the present invention with the cover removed and particularly illustrating the balance pan and the means of rotation.

FIG. 2 is an illustration of the lower portion 13 of the content analyzer 10 with the cover portions removed. The content analyzer 10 includes a source of microwave radiation shown as the magnetron 20. Although a magnetron is a good source in terms of its combination of function and relative cost, those familiar with the propagation of microwaves will recognize that the source could also consist of a klystron, a solid state device or a switching power supply. In this regard, the use of a switching power supply is set forth in commonly assigned U.S. patent application Ser. No. 09/063,545 filed Apr. 21, 1998 for "Continuously Variable Power for Microwave Assisted Chemistry" (now U.S. Pat. No. 6,084,226), the contents of which are incorporated entirely herein by reference. A waveguide (which is covered by other elements in the orientation of FIG. 2) connects the source 20 of microwave radiation with the cavity. The cavity is likewise described in more detail in other co-pending applications that have already been incorporated, particularly Ser. No. 09/396,129. A balance 21 has at least its pan 22 positioned in the cavity. The pan 22 does not need to be physically solid. In a preferred embodiment illustrated in FIGS. 2 and 3, the pan is formed of a circular support portion 23 with several struts 24 maintaining the support 23 on the vertical shaft 25 of the balance 21. In preferred embodiments, the balance is a force restoration balance with an accuracy of ±0.1 mg.

FIG. 2 also illustrates that the portion of the balance that is in the cavity does not interfere with the propagation of microwaves in the cavity or the modes of microwaves in the cavity while the analyser is in operation. Accordingly, in preferred embodiments, the balance pan 22 including the struts 24, the circular support 23 and the appropriate portions of the shaft 25, are formed of materials that do not interfere with or absorb microwaves. Stated differently, they are preferably formed of materials that are transparent to microwave radiation. Generally speaking, such materials will consist of appropriate polymers or other non-metallic materials of which many are well known to those of ordinary skill in the art, and can be selected without undue experimentation. To the extent that more portions of the balance can be formed of materials that do not interfere with microwaves, or can be otherwise shielded from microwaves, those portions can likewise extend into the cavity. In present embodiments, it appears to be most useful, however, to have only the balance pan 22 and a small portion of the shaft 25 extend into the cavity, with the remainder of the balance being shielded from the cavity.

Figure 3:
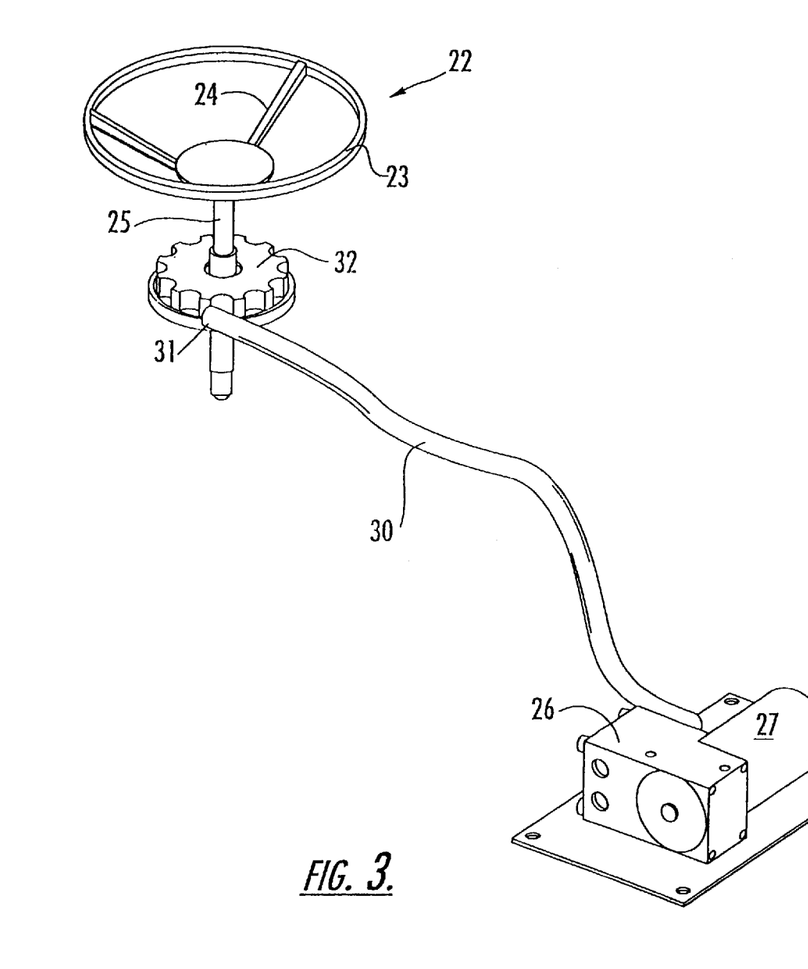
FIG. 3 is a view of the balance pan and the means for rotating it taken from FIG. 2 in simplified fashion.

FIGS. 2 and 3 further illustrate that the rotation of the shaft and the pan 22 are best accomplished in preferred embodiments by the use of an air pump 26 and its associated motor 27. A hose 30 carries a stream of air to its terminal portion 31 adjacent to an impeller 32 that is coaxially mounted on the shaft 25. The airflow from the terminal portion 31 of the hose 30 turns the impeller 32 which, being fastened to the shaft 25, rotates the balance pan 22 in a desired fashion. It will be understood that there are a number of appropriate engineering solutions for rotating the pan 22 with the desired speed and while maintaining the desired balance accuracy. These will be recognized by those of skill in this art and can be designed and built without undue experimentation and are equivalents of the design illustrated herein, which should be considered illustrative, rather than limiting, of the method in which the pan 22 can be rotated. In general, however, the air and impeller drive of the preferred embodiment provides a non-contact technique that avoids interfering with the balance. Magnetic drives will work, but must be carefully shielded from the microwave radiation in the cavity. In turn, if a magnetic drive is used, it must be shielded from the balance if the balance is sensitive to a magnetic field. Mechanical drives can be used, but are more difficult to integrate with the weighing functions of the balance.

The apparatus content analyzer 10 of the present invention can also include an appropriate microprocessor. FIG. 2 illustrates a processor at 34 mounted on an appropriate board (or card) 35. The processor 34 can be any appropriate processor that can carry out the intended functions. Specifically, the processor 34 typically receives output information from the balance 21. By comparing the output from the balance 21 against an internal clock, is able to calculate the weight loss over a time as a sample is dried in the content analyzer 10. There are several well-known relationships between drying time and moisture content that the processor can use to determine the end point of a given sample. In a conventional method, the processor 34 can identify when the weight has remained constant for a sufficient period of time to indicate that the sample has no more moisture to lose and that the run can be ended. In other techniques (e.g. U.S. Pat. No. 4,438,500), the processor can track the weight loss along a generally well understood algebraic curve, and predict an appropriate end point even before the sample has completely dried. In a simple, but effective technique, the sample is heated for a predetermined and fixed time. This fixed-time technique appears to be particularly satisfactory for low moisture-content samples. These and other techniques for determining the end point of content analysis, and the manner of using a processor to assist in the end point determination, are generally well understood in the art and will not be discussed in detail herein. Those of ordinary skill in this art can produce such programs and select such processors without undue experimentation. Generally speaking, however, the processor 34 will be the same as or very similar to those used in personal computers.

The other components of the card 35 can be selected as desired or necessary, and will not be discussed in detail, other than to note that the card 35 includes appropriate input and/or output ports (e.g. serial, parallel, USB) 36, 37, and 40.

FIG. 2 also illustrates a portion 41 of the overall housing, as well as a shielding portion 42 that separates certain of the electronic devices such as the card 35 from the balance 21 and the source 20. These physical structures are generally conventional, and can be formed of any appropriate material that does not otherwise interfere with the operation of the content analyzer 10. Appropriate materials and their design and manufacture are well understood in the art and can be produced by those of ordinary skill without undue experimentation.

Figure 4:
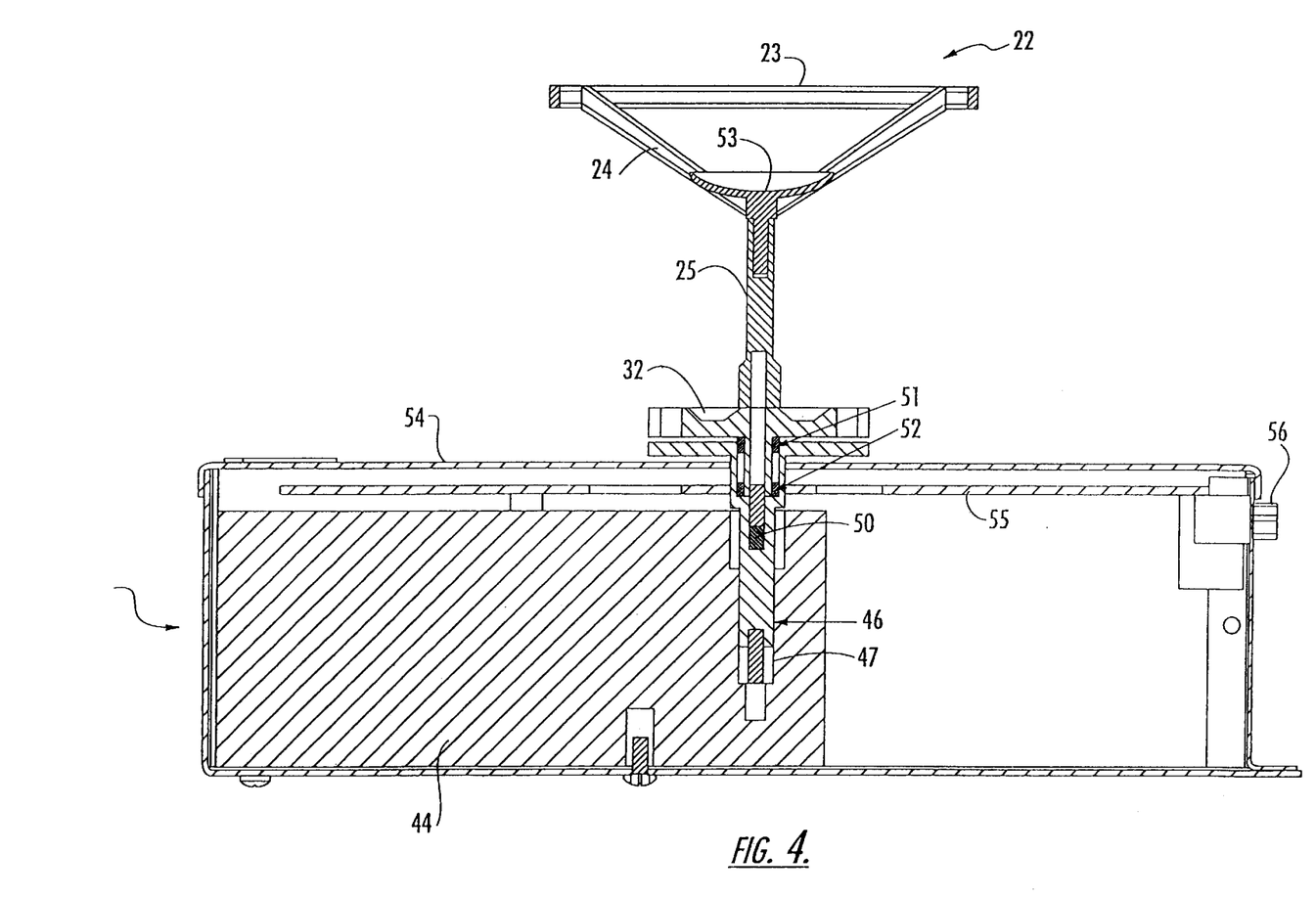
FIG. 4 is a cross sectional view of the rotating balance pan according to the present invention.

FIG. 4 is a cross sectional view of one embodiment of the invention showing the manner in which the balance pan 22 is supported for rotation.

FIG. 4 is a cross-sectional view of the balance pan and rotation mechanism according to the present invention. As in FIGS. 2 and 3, the balance pan is broadly designated at 22, with the circular support 23 and struts 24 also illustrated along with the shaft 25. In FIG. 4, the balance is again broadly designated at 21 with its mechanism being indicated by the shaded rectangle 44. The turbine or impeller 32 is mounted on the shaft 25. In order to adapt the balance pan for rotation, the balance includes a balance stem adapter 46, which is connected by setscrews 47 and 50 to both the balance mechanism 44 and the impeller 32. Two respective sets of bearings 51 and 52 provide the support for the impeller to rotate while the balance stem adapter 46 keeps it maintained with respect to the rest of the balance mechanism 44 to provide the appropriate weight measurements.

In preferred embodiments, the balance pan 22 includes the drip tray illustrated at 53, which catches appropriate liquids that may drop from the sample on the balance pan and prevents them from interfering with the rotation or weight measurement functions of the balance 21. In preferred embodiments, the balance stem 25 is formed of a material that does not otherwise interfere with or respond to the microwave radiation in the cavity. Preferred materials include any polymer that offers the required structural integrity and does not absorb microwave radiation. Such materials are well known in this art and can be selected by those of ordinary skill without undue experimentation. FIG. 4 also illustrates a balance cover 54, a circuit board 55 for the balance, and various input/output or power ports 56 for the balance.

Figure 5:
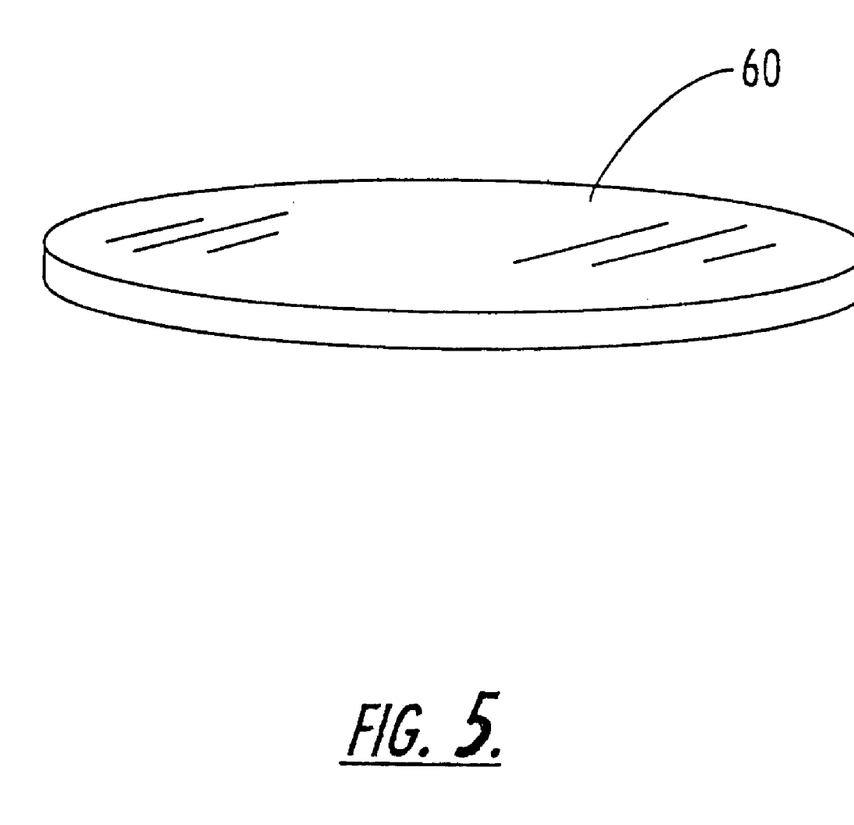
FIG. 5 is a susceptor according to the present invention.

FIG. 5 illustrates in schematic fashion a susceptor 60 according to the present invention. In preferred embodiments, the susceptor 60 is formed of a first material dispersed with a second material. The first material is the material which generates heat in response to microwave radiation and the second material is generally less responsive or non-responsive to microwave radiation, but conductively heated by the first material so that exposing the susceptor 60 to microwave radiation evenly heats the pad and any sample on the pad. In preferred embodiments, the susceptor 60 is a circular disc approximately 4 ⅜ inch in diameter by about ⅟₁₀ inch in thickness. These are, of course, exemplary measurements (and a circle is an exemplary shape) and are not limiting of the susceptor of the present invention.

In the most preferred embodiments, the susceptor 60 is formed of three materials. In such embodiments, the third material is similar, but nonidentical to the first material. The third material is similar in that it absorbs microwaves and generates heat in response, but in a somewhat different manner than does the first material. To date, it has been empirically observed that a combination of two such different, but absorbing materials provides far more even heating of the susceptor—and thus far more even heating of the sample—than does the use of one material alone. The absorbing materials are preferably present in the minimum amount that provides the pad with a rapid and uniform response to microwave radiation. In the size described above the pad 60 is typically formed of a combination of 4 grams (g) of graphite, 5 g of silicon carbide (SiC), 33 g of silicone resin and a few drops of a hardening catalyst for the silicone resin. This corresponds to about 12 percent by weight silicon carbide, about 10 percent by weight of graphite, and about 78 percent by weight of the silicone rubber.

Those of ordinary skill in the art will recognize that in terms of the sole function of responding to microwaves, solid silicon carbide can be used as a susceptor material as can solid graphite, or even other materials such as garnet (e.g., silicate materials). Each of these have particular disadvantages. For example, graphite is extremely messy and tends to produce a great deal of carbon dust under almost any circumstances. Thus, susceptors formed of solid graphite heat the sample, but raise a number of additional handling problems that make it's use disadvantageous.

Similarly, solid silicon carbide likewise responds to microwave radiation. Silicon carbide is, however, notoriously difficult to manufacture in large wafer sizes and its degree of response to microwave radiation is relatively high, meaning that a susceptor formed entirely of silicon carbide has to be extremely thin to avoid overheating sensitive samples while still becoming heated in a reasonably short period of time. Additionally, temperature control of susceptors formed entirely of silicon carbide tends to be difficult. Furthermore, thin pads of silicon carbide are difficult and expensive to manufacture and hard to handle.

By blending these materials in the manner of the present invention, the resulting pad is more durable, costs less to manufacture, is more easily formed into a disk, is easier to clean and reuse, and heats faster. Silicon carbide and graphite also absorb the magnetic and electric components of electromagnetic fields slightly differently from one another, so that their combination enhances the overall response of the susceptor.

Silicone rubber is a material of choice because it is generally safe, non-toxic, non-volatile, physically easy to work with, resistant to physical and chemical degradation even at the expected operating temperatures, easy to mold quickly, and blends well with silicon carbide, graphite, and garnet.

Experimental—Heating Profiles

Round susceptor pads according to the present invention were formed using garnet, silicon carbide, graphite, and blends of these materials in proportions by weight that were the same or similar to those set forth above with respect to the silicone rubber. The pads were then exposed to microwave radiation and the temperature of each pad was measured at the edge (i.e., near the circumference) of the pad, at the center of the pad, and at a point midway between the center and the edge. The results were as follows (temperatures are in degrees Centigrade):

| Material | Center | Midpoint | Edge |
| --- | --- | --- | --- |
| Garnet | 117 | 130 | 140 |
| SiC | 114 | 89 | 79 |
| Graphite | 115 | 128 | 113 |
| SiC:Garnet (1:1) | 119 | 108 | 102 |
| SiC:Garnet (4:1) | 115 | 118 | 110 |
| SiC:Graphite (1:1) | 112 | 120 | 116 |

These results demonstrate that an appropriate blend of two microwave-responsive materials provides more uniform and consistent heating across the susceptor pad, and that the preferred blend of SiC and graphite provided the most consistent results.

Analysis of Powdered Milk

Samples of powdered nonfat dry milk were obtained from several suppliers and were tested using the apparatus and method of the present invention. As noted above, the low moisture content of powdered milk makes it particularly difficult to successfully analyze using conventional microwave techniques. Each sample weighed approximately 4 grams and two portions of each sample were tested. The analysis was carried out for about 5 minutes, which provided sufficient time for the weight of each sample to reach a constant value, thus indicating dryness. In each case the temperature was maintained at between about 115° and 120° C. using the temperature control techniques and apparatus of the invention. The results are summarized in the following table in which the respective supplier provided the standard analysis of each sample:

| Sample | Microwave Analysis | Standard Analysis |
| --- | --- | --- |
| 1 | 3.28 | 3.3 |
| 1 | 3.30 | 3.3 |
| 2 | 3.74 | 3.9 |
| 2 | 3.86 | 3.9 |

-continued

| Sample | Microwave Analysis | Standard Analysis |
|---|---|---|
| 3 | 3.62 | 3.6 |
| 3 | 3.53 | 3.6 |
| 4 | 3.57 | 3.5 |
| 4 | 3.40 | 3.5 |
| 5 | 4.40 | 4.48 |
| 5 | 4.45 | 4.48 |

The results demonstrate that the invention provides a moisture content analysis technique that is as accurate as current standard analysis techniques.

As other advantages of the invention, the rotation of the sample, and preferably the sample and susceptor, tends to heat the sample more quickly and more uniformly. These advantages in turn enhance the temperature measurement, feedback, and control aspects of the apparatus and method. The thermal mass of the susceptor also helps heat the sample more efficiently, and gives better process control because the heat loss is slow rather than rapid. The method of the invention also comprises measuring the temperature of the susceptor while the susceptor is rotating on the balance pan, and then using the measured temperature to control or moderate the microwave radiation sent into the cavity by the source. An appropriate infrared temperature measuring technique is set forth in co-pending and commonly assigned U.S. patent application Ser. No. 09/156,086 incorporated earlier herein. As discussed therein, an infrared temperature monitor is particularly preferred because it tends to measure only heat being admitted by the sample or the sample pad. Using the present invention, the rotation and the equilibrium that rotation brings to bear helps keep the temperature of the susceptor and the sample the same. Thus, the invention produces a very accurate temperature measurement, which in turn provides for very accurate temperature control. Additionally, because microwaves are generally considered to be at quite different frequencies than infrared radiation, the presence of large amounts of microwaves in the cavity does not interfere with the infrared detection technique. Generally speaking, the processor 34 referred to earlier herein, can likewise handle the appropriate data from the temperature measurement, and use it to moderate the radiation either from the source 20 or that can be allowed to travel from the source to the cavity.

In actual use, the balance is set to tare with the susceptor on the pan. The sample is then added to the susceptor, the weight is recorded, and then the microwaves are applied. The temperature of the sample and susceptor are monitored constantly, and the measured temperature is used to moderate the microwave power applied in order to keep the sample and susceptor at a controlled temperature that is usually preselected based upon the material being dried (the general characteristics of which are usually known). For example, in the pharmaceutical industry certain standardized tests must be carried out a t specific temperatures in order to be valid or certified or both.

The sample and susceptor are kept at the controlled temperature for a fixed period of time (again based at least in part on the general characteristics of the material being dried) after which the sample is reweighed and the moisture content calculated based on the weight loss and sample mass.

The invention can also preferably incorporate the techniques of previously incorporated application Ser. No. 09/398,130 which improves the accuracy of weight measurements by adjusting apparent weight to true weight by considering weight bias caused by air density gradients. As set forth therein, this is preferably carried out by the steps of measuring an apparent weight of a substance, concurrently measuring a surface temperature of the substance, concurrently measuring an ambient air temperature surrounding the substance, predicting buoyancy forces acting upon the substance based on the surface temperature of the substance and the ambient air temperature surrounding the substance, and determining a true weight of the substance by correcting the apparent weight of the substance by the predicted buoyancy forces acting upon the substance.

The invention has been described in detail, with reference to certain preferred embodiments, in order to enable the reader to practice the invention without undue experimentation. A person having ordinary skill in the art will readily recognize that many of the components and parameters may be varied or modified to a certain extent without departing from the scope and spirit of the invention. Furthermore, titles, headings, or the like are provided to enhance the reader's comprehension of this document and should not be read as limiting the scope of the present invention.

That which is claimed is:

1. A method of microwave assisted content analysis, the method comprising:

applying microwave radiation to a sample on a sample pad that is thermally responsive to microwave radiation and on a balance while, concurrently rotating the sample and sample pad while the microwave radiation is being applied; and while, concurrently weighing the sample on the balance; and while concurrently measuring the temperature of the rotating sample and pad; and moderating the applied microwave radiation in response to the measured temperature.

2. A content analysis method according to claim 1 comprising maintaining a balance accuracy of ±10 milligrams while concurrently weighing and rotating the sample under the applied microwave radiation.

3. A content analysis method according to claim 1 comprising maintaining a balance accuracy of ±1 milligram while concurrently weighing and rotating the sample under the applied microwave radiation.

4. A content analysis method according to claim 1 comprising maintaining a balance accuracy of ±0.1 milligram while concurrently weighing and rotating the sample under the applied microwave radiation.

5. A content analysis method according to claim 1 comprising rotating the sample and sample pad in a substantially horizontal plane.

6. A content analysis method according to claim 5 comprising rotating the sample pad at speed of rotation that is sufficient to maintain an equilibrium temperature or equilibrium rate of temperature change in a sample thereon, while less than a speed at which the sample would become dislodged from the pad or at which the desired accuracy of the balance would be reduced.

7. A content analysis method according to claim 6 comprising rotating the sample pad at a speed of less than 30 rpm.

8. A content analysis method according to claim 6 comprising rotating the sample pad at a speed of between about 5 and 20 rpm.

9. A content analysis method according to claim 1 wherein the step of applying microwave radiation to the sample comprises:

generating microwaves from a source;

transmitting the microwaves from the source to a waveguide in communication with the source;

transmitting the microwaves from the waveguide to a cavity that contains the sample.

10. A content analysis method according to claim 9 wherein the step of moderating the microwave radiation comprises moderating the radiation produced by the microwave source.

11. A content analysis method according to claim 9 wherein the step of moderating the microwave radiation comprises moderating the transmission of microwaves between the source and the cavity.

12. A content analysis method according to claim 1 wherein the step of measuring the temperature comprises measuring the infrared radiation emitted by the sample and pad.

13. A content analysis method according to claim 1 and further comprising concurrently measuring the ambient air temperature surrounding the sample and susceptor pad;

predicting buoyancy forces acting upon the sample and pad based on the surface temperature of the sample and pad and the ambient air temperature surrounding the sample and pad; and determining a true weight of the substance by correcting the apparent weight of the substance by the predicted buoyancy forces acting upon the substance.

14. An apparatus for microwave-assisted content analysis, said apparatus comprising:

a source of microwave radiation;

a cavity in microwave communication with said source;

a balance with at least its pan in said cavity;

means for rotating said balance pan within said cavity while concurrently measuring the weight of a sample on said pan and while concurrently applying microwave radiation from said source;

means for measuring the temperature of the sample while the sample is rotating and while its weight is being measured and while microwave radiation is being applied; and means for moderating the microwave radiation in said cavity in response to the measured temperature.

15. A microwave apparatus according to claim 14 wherein the portion of said balance in said cavity does not interfere with the propagation or modes of microwaves in said cavity.

16. A microwave apparatus according to claim 14 wherein said microwave source is selected from the group consisting of magnetrons, klystrons, solid state devices, and switching power supplies.

17. A microwave apparatus according to claim 14 and further comprising a waveguide between said source and said cavity, and in microwave communication with both said source and said cavity.

18. A microwave apparatus according to claim 14 wherein said balance comprises a force restoration balance.

19. A microwave apparatus according to claim 14 wherein said balance maintains an accuracy within 10 milligrams while said balance pan is rotating.

20. A microwave apparatus according to claim 14 wherein said balance maintains an accuracy within 1 milligram while said balance pan is rotating.

21. A microwave apparatus according to claim 14 wherein said balance maintains an accuracy within 0.1 milligram while said balance pan is rotating.

22. A microwave apparatus according to claim 14 wherein said rotation means can provide a speed of rotation from zero to about 30 rpm.

23. A microwave apparatus according to claim 14 wherein said temperature measurement means comprises an infrared detector.

24. A microwave apparatus according to claim 14 wherein said moderating means comprises means for moderating the microwaves produced by said source.

25. A microwave apparatus according to claim 14 wherein said moderating means comprises means for moderating the transmission of microwaves between said source and said cavity.

26. A microwave apparatus according to claim 14 and further comprising:

means for concurrently measuring the ambient air temperature surrounding the sample and susceptor pad;

means for predicting buoyancy forces acting upon the sample and pad based on the surface temperature of the sample and pad and the ambient air temperature surrounding the sample and pad; and means for determining a true weight of the substance by correcting the apparent weight of the substance by the predicted buoyancy forces acting upon the substance.

* * * * *